United States Patent [19]
Trubiano et al.

[11] Patent Number: 6,086,917
[45] Date of Patent: *Jul. 11, 2000

[54] TABLET CONTAINING AN ENZYMATICALLY CONVERTED STARCH DERIVATIVE ENCAPSULATING AGENT

[75] Inventors: Paul Trubiano, Somerville; Dennis Boyd, Neshanic Station, both of N.J.

[73] Assignee: National Starch and Chemical Investment Holding Corporation, Wilmington, Del.

[*] Notice: This patent is subject to a terminal disclaimer.

[21] Appl. No.: 09/178,087

[22] Filed: Oct. 23, 1998

[51] Int. Cl.[7] .............................. A61K 9/20; A61K 9/46; A61K 9/00; A01N 25/00; C08B 31/60
[52] U.S. Cl. ..................... 424/465; 424/466; 424/405; 424/408; 424/400; 536/105; 536/106; 536/102
[58] Field of Search ................................ 424/465, 466, 424/405, 408, 400; 536/105, 106, 102

[56] References Cited

U.S. PATENT DOCUMENTS

| | | | |
|---|---|---|---|
| 3,455,838 | 7/1969 | Marotta et al. | 252/316 |
| 4,035,235 | 7/1977 | Richards et al. | 195/31 R |
| 4,689,235 | 8/1987 | Barnes et al. | 426/89 |
| 4,845,035 | 7/1989 | Fanta et al. | 435/178 |
| 5,185,176 | 2/1993 | Chiu | 426/651 |
| 5,194,284 | 3/1993 | Chiu et al. | 426/589 |
| 5,445,950 | 8/1995 | Kobayashi et al. | 435/99 |
| 5,468,286 | 11/1995 | Chiu et al. | 106/210 |

FOREIGN PATENT DOCUMENTS 08-283303  10/1996  Japan .............................. C08B 31/04

*Primary Examiner*—Thurman K. Page
*Assistant Examiner*—Todd D Ware
*Attorney, Agent, or Firm*—Karen G. Kaiser

[57] ABSTRACT

The present invention is directed to a tablet, particularly a pharmaceutical dosage form, which contains an encapsulating agent comprising a modified starch which is prepared by enzymatic hydrolysis of a starch molecule after the preparation of a starch derivative containing a hydrophobic group or both a hydrophobic and a hydrophilic group, particularly octenyl succinic anhydride starch hydrolyzed by β-amylase or glucoamylase. Such starch allows for good compressibility and hardness of a pharmaceutical dosage form. In addition, the starch may consistently allow for high load and retention of a variety of active agents as well as oxidative resistance.

16 Claims, No Drawings

TABLET CONTAINING AN ENZYMATICALLY CONVERTED STARCH DERIVATIVE ENCAPSULATING AGENT

BACKGROUND OF THE INVENTION

The present invention relates to a tablet, particularly a pharmaceutical dosage form, containing an encapsulating agent comprising a modified starch which is prepared by enzymatic hydrolysis of a starch molecule after the preparation of a starch derivative containing a hydrophobic group or both a hydrophobic and a hydrophilic group.

U.S. Pat. Nos. 4,977,252 and 5,185,176 issued to Chiu disclose starch derivatives containing a hydrophobic or both a hydrophobic and a hydrophilic group which have been enzymatically degraded by exo-enzymes. These modified starches are useful as emulsifiers.

Compressed tablets are well-known, particularly in the pharmaceutical industry. Known methods of tabletting include direct compression and wet or dry granulation followed by compression. Tablet formulations characteristically should be free flowing, cohesive and lubricating. Sometimes, it is desired to encapsulate a component of the tablet and gelatin is considered as a standard encapsulating agent in many industries.

However, consumers may desire products which do not contain gelatin for a variety of reasons including dietary to meet strict Kosher, Halal or vegetarian standards. Many consumers also want to avoid bovine products because of the current scare over Bovine Spongiform Encephalopathy (Mad Cow Disease). Further, gelatin is an expensive excipient and its replacement is desirable to reduce the cost of the product.

It is known in the art that certain starches are excellent encapsulating agents. However, as starches are generally used as disintegrants, impeding compression and hardness of the tablet, starch encapsulating agents are not generally used in significant quantities in tablets. Hardness is necessary in a tablet as it provides resistance to chipping, abrasion, and breakage under conditions of storage, transportation, and handling prior to consumer consumption.

Other encapsulating agents are also known in the art such as gum arabic, dextrins, arabinogalactan, gum acacia, casein, carboxymethyl cellulose, tragacanth, karaya, sodium alginate, and tannin. However, none of these encapsulants allow for good compressibility while providing high load and retention of the active agent and oxidative resistance.

Surprisingly, it has now been discovered that the present invention which uses an encapsulating agent comprising a modified starch, prepared by enzymatically converting a starch after the preparation of a starch derivative containing a hydrophobic group or a hydrophobic and a hydrophilic group, allows similar compressibility characteristics and resultant hardness to gelatin in a tablet formulation. In addition, the starch may consistently allow for high load and retention of a variety of active agents as well as oxidation resistance.

SUMMARY OF THE INVENTION

The present invention is directed to a tablet, particularly a pharmaceutical dosage form, which contains an encapsulating agent comprising a modified starch which is prepared by enzymatic hydrolysis of a starch molecule after the preparation of a starch derivative containing a hydrophobic group or both a hydrophobic and a hydrophilic group. Such starch allows for good compressibility and hardness of a tablet. In addition, the starch may consistently allow for high load and retention of a variety of active agents as well as oxidative resistance.

DETAILED DESCRIPTION OF THE INVENTION

The present invention is directed to a tablet, particularly a pharmaceutical dosage form, which contains an encapsulating agent comprising a modified starch which is prepared by enzymatic hydrolysis of a starch molecule after the preparation of a starch derivative containing a hydrophobic group or both a hydrophobic and a hydrophilic group. Such starch allows for good compressibility and hardness of a tablet. In addition, the starch may consistently allow for high load and retention of a variety of active agents as well as oxidative resistance.

All starches and flours are suitable for use herein and may be derived from any native source. A native starch or flour, as used herein, is one as it is found in nature, including those developed by plant breeding, and bioengineered starches. Typical sources for the starches and flours are cereals, tubers, roots, legumes and fruits. The native source can be corn, pea, potato, sweet potato, banana, barley, wheat, rice, sago, amaranth, tapioca, arrowroot, canna, sorghum, and waxy or high amylose varieties thereof. As used herein, the term "waxy" is intended to include a starch or flour containing at least about 95% by weight amylopectin and the term "high amylose" is intended to include a starch or flour containing at least about 45% by weight amylose. In particular, corn, waxy maize, tapioca, potato, and rice are useful in the present invention.

Also included as useful base starch materials are the conversion products derived from any of the above starches including fluidity or thin-boiling starches prepared by oxidation, α-amylase conversion, mild acid hydrolysis or heat dextrinization, and derivatized starch such as ethers and esters.

A particularly useful starch base is a gelatinized starch, that is a precooked, non-granular starch, and also may be a fluidity starch converted by mild acid degradation or heat dextrinization methods that are well known in the art. For example, see Rutenberg, "Starch and Its Modifications," Handbook of Water-Soluble Gums and Resins, Davidson, Editor, McGraw-Hill, Inc., New York, N.Y. 1980, pp.22–36. A combination of one or more of these conversion techniques may be used. The conversion is typically carried out before treatment with a hydrophobic or a hydrophobic/hydrophilic reagent and before the enzyme treatment. If desired, the starch base may be converted by treatment with an α-amylase enzyme to produce a fluidity starch in the manner disclosed in U.S. Pat. No. 4,035,235. Where a high viscosity system is desired, it is not necessary to convert the base starch.

The starch may be derivatized by treatment with any reagent or combination of reagents which contributes encapsulation properties to the starch. The reagent must contain a hydrophobic moiety and may contain a hydrophilic moiety. The hydrophobic moiety should be an alkyl or alkenyl group which contains at least five carbon atoms, or an aralkyl or aralkenyl group which contains at least six carbon atoms, particularly up to about twenty-four carbon atoms. The hydrophilic moiety may be contributed by the reagent or the starch's own hydroxyl groups may serve as the hydrophilic moiety and the reagent may contribute only the hydrophobic moiety.

Any process for derivatizing starch which yields the desired blend of hydrophobic or hydrophobic and hydrophilic functions on the starch molecule and thereby yields stable encapsulation properties may be used to prepare the modified starch of the present invention. Suitable derivatives and methods for producing them are known in the art and disclosed in U.S. Pat. No. 4,626,288 which is incorporated herein by reference. In a particularly useful embodiment, the starch is derivatized by reaction with an alkenyl cyclic dicarboxylic acid anhydride by the method disclosed in U.S. Pat. Nos. 2,613,206 and 2,661,349, incorporated herein by reference, or propylene oxide, more particularly by reaction with octenylsuccinic anhydride.

Where a low viscosity is desirable, a particularly useful embodiment is an octenyl succinic half ester derivative of an amylopectin containing starch, such as waxy maize, which has been converted to a water fluidity (WF) of up to about 60. Water fluidity is an empirical test of viscosity measured on a scale of 0–90 wherein fluidity is the reciprocal of viscosity. Water fluidity of starches is typically measured using a Thomas Rotational Shear-type Viscometer (commercially available from Arthur A. Thomas CO., Philadelphia, Pa), standardized at 30° C. with a standard oil having a viscosity of 24.73 cps, which oil requires 23.12±0.05 sec for 100 revolutions. Accurate and reproducible measurements of water fluidity are obtained by determining the time which elapses for 100 revolutions at different solids levels depending on the starch's degree of conversion: as conversion increases, the viscosity decreases. In a particularly useful embodiment, the converted starch is treated with from about 0.1% to about 3.0% for food products, and at least about 0.1% for other products, of octenyl succinic anhydride. In the alternative, a hydroxypropyl octenyl succinic derivative may be used.

For other products, any degree of substitution or level of conversion that results in the desired viscosity and encapsulation properties may be employed. For example, U.S. Pat. No. 4,035,235 disclosed a suitable embodiment comprising a method for producing a hydrophobic derivative of starch to be used as an alternative to gum arabic in encapsulating water insoluble substances, such as volatile flavoring oils and perfumes.

After derivatizing the starch, it is further enzymatically hydrolyzed by at least one enzyme capable of cleaving the 1,4-linkages of the starch molecule from the non-reducing ends to produce mono- and/or di-saccharides to provide high oxidation resistance, while maintaining substantially high molecular weight portions of the starch base to provide encapsulating properties. The enzymes useful in the present invention thus include, but are not limited to, β-amylase, glucoamylase, maltogenase, pullulanase, exo-alpha-1,4-glucosidase, exo-1,4-alpha-D-glucan maltotetrahydrolase, and exo-1,4-alpha-D glucan maltohexahydrolase, particularly β-amylase, and glucoamylase.

The enzymatic hydrolysis of the starch base is carried out using techniques known in the art. The amount of enzyme used is dependent upon the enzyme, i.e., type, source and activity, and base material used as well as the amount of hydrolysis desired. Typically, the enzyme is used in an amount of from about 0.01 to about 1.0%, particularly from about 0.01 to 0.3%, by weight of the starch.

The optimum parameters for enzyme activity will vary depending upon the enzyme used. The rate of enzyme degradation depends upon factors known in the art, including the type of enzyme used, enzyme concentration, substrate concentration, pH, temperature, the presence or absence of inhibitors, and the degree and type of modification. These parameters may be adjusted to optimize the digestion rate of the starch base.

The starch may be gelatinized before enzyme hydrolysis. The gelatinization process unfolds the starch molecules from the granular structure, thereby permitting the enzyme to more easily and uniformly degrade the starch molecules.

Generally the enzyme treatment is carried out in an aqueous or buffered slurry at a starch solids level of about 10 to about 40%, depending upon the base starch being treated. A solids level of from about 15 to 35% is particularly useful, from about 18 to 25% more particularly useful, in the instant invention. In the alternative, the process may utilize an enzyme immobilized on a solid support.

Typically, enzyme digestion is carried out at the highest solids content feasible without reducing reaction rates in order to facilitate any desired subsequent drying of the starch composition. Reaction rates may be reduced by high solids content as agitation becomes difficult or ineffective and the starch dispersion becomes more difficult to handle.

The pH and temperature of the slurry should be adjusted to provide effective enzyme hydrolysis. These parameters are dependent upon the enzyme to be used and are known in the art. In general, a temperature of about 22 to about 65° C. is used, particularly from about 50 to about 62° C. In general, the pH is adjusted to about 3.5 to about 7.5, particularly from about 4.0 to about 6.0, using techniques known in the art.

The enzyme reaction is continued until a dextrose equivalent of at least about 20 and up to about 80, particularly about 20 to about 50, has been achieved, or until the desired end point (i.e., sufficient degradation to provide the desired functionality for the particular application) has been reached. The end point may be determined by a change in viscosity, by reducing sugar content (such as measured by dextrose equivalents), or by any other method known in the art for measuring the level of enzyme degradation of the starch molecule. In general, the enzyme reaction will take from about 0.1 to about 24 hours, particularly about 0.5 to about 4 hours. The time of the reaction is dependent upon the type of starch and enzyme used, the amount of enzyme used, and the reaction parameters of solids percent, pH, and temperature.

The enzyme degradation is then terminated by any technique known in the art such as acid or base deactivation, heat deactivation, ion exchange, and solvent extraction. For example, acid deactivation may be accomplished by adjusting the pH to lower than 2.0 for at least 30 minutes or heat deactivation may be accomplished by raising the temperature to about 85 to about 95° C. and maintaining it at that temperature for at least about 10 minutes to fully deactivate the enzyme. Heat deactivation is not suitable if a granular product is desired as the heat necessary to deactivate the enzyme will generally also gelatinize the starch.

The resultant solution is typically adjusted to the desired pH according to its intended end use. In general, the pH is adjusted to from about 3.0 to about 7.5, particularly from about 3.5 to about 6.5, using techniques known in the art. The modified starch is then typically dried using methods known in the art, particularly spray drying. However, the modified starch may also be used as a liquid concentrate.

The resulting starch is characterized by a relatively low viscosity, moderately high dextrose equivalent, neutral taste, and by its unique functionality as an encapsulating agent.

The viscosity of the resultant starch should be less than about 30 seconds, particularly from about 8 to about 25 seconds, more particularly from about 8 to about 15 seconds as measured by the funnel method. Viscosity is an important parameter in contributing to efficient encapsulation.

To measure the viscosity of the starch by the funnel method, the starch dispersion to be tested is adjusted to 19% or 25% (w/w) measured by refractometer. The temperature of the dispersion is controlled at 22° C. A total of 100 ml of the starch dispersion is measured into a graduated cylinder. It is then poured into a calibrated funnel while using a finger to close the orifice. A small amount is allowed to flow into the graduate to remove any trapped air and the balance is poured back into the funnel. The graduated cylinder is then inverted over the funnel so that the contents draw (flow) into the funnel while the sample is running. Using a timer, the time required for the 100 ml sample to flow through the apex of the funnel is recorded.

The glass portion of the funnel is a standard 58°, thick-wall, resistance glass funnel whose top diameter is about 9 to about 10 cm with the inside diameter of the stem being about 0.381 cm. The glass stem of the funnel is cut to an approximate length of 2.86 cm from the apex, carefully fire-polished, and refitted with a long stainless steel tip with is about 5.08 cm long with an outside diameter of about 0.9525 cm. The interior diameter of the steel tip is about 0.5952 cm at the upper end where is attached to the glass stem and about 0.4445 cm at the outflow end with the restriction in the width occurring at about 2.54 cm from the ends. The steel tip is attached to the glass funnel by means of a Teflon tube. The funnel is calibrated so as to allow 100 ml of water to go through in six seconds using the above procedure.

The resultant starch should have a dextrose equivalent of at least about 20 and up to about 80. When glucoamylase is used to hydrolyze the derivatized starch, the DE is particularly from about 30 to about 50. When β-amylase is used, the DE is particularly from about 20 to about 50, more particularly from about 25 to about 38. Dextrose equivalent (DE) is defined as the reducing power of the hydrolyzate. Each starch molecule has one reducing end: therefore DE is inversely related to molecular weight. The DE of anhydrous D-glucose is defined as 100 and the DE of unhydrolyzed starch is virtually zero.

In the alternative, the derivatized starch may be blended with sugars, for example mono- di- or oligo-saccharides or maltodextrins, instead of producing the sugars in situ. The mono- di-, and oligo-saccharides include all saccharides of up to about 10 glucose units, particularly those of up to about three glucose units, such as glucose, fructose, galactose, maltose, isomaltose, sucrose, lactose, raffinose, stachyose, fructosylsucrose, and maltooligosaccharides, particularly glucose, fructose, and maltose. The maltodextrins include those with a dextrose equivalent of from about 2 to about 50, particularly from about 5 to about 15.

The resultant starch/sugar blend should have a relatively high percent of sugars measured as glucose, at least about 20 and up to about 80%. When glucoamylase is used to hydrolyze the derivatized starch, the resultant starch should have a sugar level particularly from about 30 to about 40% sugar, more particularly from about 30 to about 35% sugar by weight. When β-amylase is used to hydrolyze the derivatized starch, the resultant starch should have a sugar level particularly from about 40 to about 60% sugar by weight.

The resultant starches (or starch/sugar blends), when used as encapsulating agents, generally have the advantages of achieving and maintaining consistently high load levels, low oil exposure, and excellent oxidation resistance.

The active agents may be encapsulated using the modified starches of the present invention and techniques known in the art, including but not limited to spray drying, extrusion, spray chilling, and fluid bed coating. For example, the starch may be dispersed in water, the active agent may be added and emulsified, and the emulsion may then be spray dried to form the encapsulated product.

When a starch/sugar blend is used, spray drying efficiencies may be decreased due to the high viscosity of the system and greater dryer deposits, particularly when mono-saccharides are used. Spray efficiencies may be increased by methods known in the art, such as using high drying towers, lightly oiling the chamber walls, or using preconditioned air in which the moisture has been substantially removed.

The active agent may be any substance which will not react with the starch system, including but not limited to vitamins, pharmaceuticals, oils, proteins, fats, flavors, colors, pesticides, catalysts, and fragrances. In particular, the modified starch of the present invention is useful for encapsulating oil-based active agents, such as botanical oils and essential oils; oil soluble vitamins, including vitamins A, D, E and K; proteins such as peptides, amino acids, and enzymes; oils soluble pesticides; and oil soluble pharmaceuticals including those with low bioavailability. The encapsulated oils may be volatile or non-volatile and are generally characterized by being water immiscible but dispersible (emulsifiable) in water in the presence of an encapsulating agent.

The encapsulated product prepared with the present encapsulating agents may achieve and maintain a relatively high load level of the active agent. The load level of the active agent realized may be greater than 30%, particularly greater than 40%, more particularly greater than 50%, by weight of the encapsulating agent. The level of active agent retained may be determined by methods known in the art such as by hydro-distillation and solvent extraction or by solvent extraction alone.

A high load level of active agent is desirable to reduce the cost of producing the final product as encapsulating agents are often expensive. Further, some encapsulating agents may contribute adverse or undesirable properties to the final system and it is thus desirable to reduce the amount of encapsulating agent used.

The load of the encapsulating agent may be limited in some instances by the processing of the end use form. For example, in a direct compression tablet, loading may be limited as high compression forces may result in leakage of the encapsulated oil, lowering the hardness of the resultant tablet and resistance to oxidation.

It is desirable not only to achieve a high load of active agent, but also to maintain it so as to enable a longer shelf life. Active agents may be volatile and/or labile. When the active agents are not encapsulated, they may be lost, producing undesirable variations of the final products as perceived by the consumer. In addition, losses of such components increase the cost of the final products since it is necessary to increase the amount of the volatile/labile component to compensate for the losses which occur, and many are expensive.

In the case of oil or an oil soluble compound as an active agent, the present encapsulating agents also retain the oil so as to provide a low surface oil. This is particularly true when glucoamylase is used to enzymatically hydrolyze the starch. The surface oil may be measured by methods known in the art such as by washing the encapsulated powder with a suitable solvent. Reduction of surface oil is important as increased surface oil indicates that the load of the active agent is not being maintained and inefficiency of encapsulation. Thus, reduction of surface oil results in a longer shelf life.

The present encapsulating agents also may provide a relatively high level of oxidation resistance, thereby prolonging storage stability of the encapsulated product and shelf life of the final product. Oxidation resistance may be measured by methods known in the art. For example, oxidation resistance of encapsulating agents containing citrus oil may be determined by using gas chromatography (GC) to measure the amount of oxidization products of limonene, such as carvone, carviol, or limonene oxide, present in the oil extracted from powders aged at 50° C. for two weeks: less than about 0.8% carvone typically indicates acceptable levels of oxidation. Oxidation resistance is important to maintain the activity of various compounds, particularly vitamins. To further increase oxidation resistance, an anti-oxidant may be added to the oil.

The encapsulated product may be used in a solid tablet-like form for a variety of applications, including detergents, foods and beverages, bath oils, agricultural products, and pharmaceuticals. The encapsulated products are particularly suitable for pharmaceutical tablets, including effervescent tablets.

The encapsulated product may generally be used at the desired level, the amount being dependent upon the amount of active agent to be incorporated, the desired hardness of the tablet, and the oxidative resistance desired. In general, the encapsulated product will be used in an amount of from about 1 to about 95% by weight of the tablet allowing for the active agent to be incorporated in an amount of from about 1 to about 60, particularly from about 10 to about 50%, by weight of the tablet.

The encapsulated product is particularly useful in a compressed tablet. The compressed tablet may be made using any method known in the art, particularly by direct compression of the tablet components. In the alternative, the tablet may be prepared by dry blending the encapsulated product with the other components of the formulation, granulating the mixture such as by fluid bed technology, roller compactor, extrusion, or high shear granulator, and dry compacting to a tablet.

Pharmaceutical excipients known in the art may be added to the pharmaceutical dosage form to impart satisfactory processing, compression, and disintegration characteristics to the formulation. Such excipients include, but are not limited to, diluents, flow enhancer, binders, lubricants and glidants, disintegrants, colors, flavors and sweetening agents. These excipients are well known in the art and are limited only by compatibility and characteristics desired.

Binders for the present invention include gelatin, microcrystalline cellulose, sugars, carboxymethyl cellulose, methyl cellulose, polyvinyl pyrrolidone, acacia, alginic acid, guar gum, hydroxypropyl methylcellulose, polyethylene oxide and ethyl cellulose.

Lubricants and glidants include talc, magnesium stearate, calcium stearate, stearic acid, glyceryl behenate, mineral oil, polyethylene glycol, sodium stearyl fumarate, stearic acid, vegetable oil, zinc stearate, and silicon dioxide.

Disintegrants suitable for the present invention include starches, algins, gums, croscarmelose, crospovidone, sodium starch glycolate, sodium laurel sulfate, microcrystalline cellulose, polacrilin potassium, and methylcellulose.

Diluents suitable for the present invention include dicalcium phosphate, calcium sulfate, lactose, cellulose, Kaolin, mannitol, sodium chloride, starch, sugars, calcium carbonate, calcium phosphate, dextrates, dextrin, dextrose, fructose, sorbitol, sucrose, and microcrystalline cellulose.

In particular, a binder is added to the tablet formulation to provide a tablet with the desired hardness. In general the hardness of the resultant tablet is at least about 3, more particularly at least about 4, most particularly at least about 6 kilopascals (kP).

If the final desired product is other than a pharmaceutical dosage form, alternative additives known to those arts may be present. For example, flavors and fragrances in a bath oil tablet or surfactants in a detergent tablet.

Upon contact with water, the moisture triggers the release mechanism, allowing the active agent to be released from the encapsulating starch. For example, upon digestion of the pharmaceutical dosage forms, the active agent is released to the body.

EXAMPLES

The following examples are presented to further illustrate and explain the present invention and should not be taken as limiting in any regard. The following analytical test was used to measure dextrose equivalents (DE) in the examples.

Determination of Dextrose Equivalents (DE)

The dextrose equivalent of starch may be determined by using the Reducing Sugars test described in Food Chemicals Codex, 4th ed., Jul. 1, 1996. Section 5, General Tests and Assays, Appendix X: Carbohydrates (Starches, Sugars, and Related Substances) or Standard Analytical Method #E-26 for Dextrose Equivalent from the Corn Refiners Association.

Example 1 - Preparation of the Derivatized Starch 500 grams of waxy maize starch were slurried in 750 ml water. The pH was adjusted to 7.5 using 3% sodium hydroxide. 15 grams of octenylsuccinic anhydride (OSA) were added in one-third increments every thirty minutes while maintaining the pH at 7.5 using 3% sodium hydroxide and constant agitation. The starch was then filtered out and washed with 750 ml water. The starch was then reslurried in 500 ml water and the pH adjusted to 5.5 with 3:1 hydrochloric acid. The starch was then filtered, washed with 750 ml water, and air dried to produce an OSA starch.

Example 2 - Preparation of the Modified Starch a. Using glucoamylase 100 grams of the OSA starch of Example 1 were slurried in 300 ml water and the pH adjusted to 5.5 using dilute hydrochloric acid. The slurry was gelatinized by jet cooking in a C1-339 jet cooker, commercially available from National Starch and Chemical Company, at 300° F., at a chamber pressure of 55 psi, and a slurry rate of 6ml/min with the steam valve open at 75% capacity.

The temperature of the starch solution was then decreased to 55° C. 0.05% glucoamylase (AMG 200 L, commercially available from Novo Nordisk) based on the weight of the starch was added and the reaction was allowed to proceed at 55° C. with constant mixing for approximately 2.5 hours until a dextrose equivalent of 36 and a viscosity of 17 sec at 25% solids and 22° C. using the funnel method. The enzyme was then deactivated by heating the dispersion to 90° C. and maintaining the elevated temperature for 30 minutes. The dispersion was then cooled to room temperature and spray dried using an inlet temperature of 200° C., an outlet temperature of 100° C. and a feed rate of 65 ml/min.

b. Using β-amylase 100 grams of the OSA starch of Example 1 were slurried in 300 ml water and the pH adjusted to 5.5 using dilute hydrochloric acid. The slurry was gelatinized by jet cooking in a C1-339 jet cooker, commercially available from National Starch and Chemical Company, at 30° F., at a chamber pressure of 55 psi, and a slurry rate of 6 ml/min with the steam valve open at 75% capacity.

The temperature of the starch solution was then decreased to 55° C. 0.2% β-amylase (Spezyme BBA 1500, commercially available from Genencor) based on the weight of the starch was added and the reaction was allowed to proceed at 55° C. with constant mixing for approximately 4 hours until a dextrose equivalent of 36 and a viscosity of 17 sec at 25% solids and 22° C. using the funnel method. The enzyme was then deactivated by heating the dispersion to 90° C. and maintaining the elevated temperature for 30 minutes. The dispersion was then cooled to room temperature and spray dried using an inlet temperature of 200° C., an outlet temperature of 100° C. and a feed rate of 65 ml/min.

c. Using a Combination of β-amylase and Pullulanase 100 grams of the OSA starch of Example 1 were slurried in 300 ml water and the pH adjusted to 5.25 using dilute hydrochloric acid. The slurry was gelatinized by jet cooking in a C1-339 jet cooker, commercially available from National Starch and Chemical Company, at 290° F., at a chamber pressure of 40 psi, and a slurry rate of 3.5 ml/min with the steam valve open at 75% capacity.

The temperature of the starch solution was then decreased to 58° C. 5.0% of pullulanase (Promozyme, commercially available from Novo) by weight of starch was added and allowed to react for approximately 18 hours with constant mixing. Then 0.1% β-amylase (Spezyme BBA 1500, commercially available from Genencor) based on the weight of the starch was added and the reaction was allowed to proceed at 58° C. with constant mixing for approximately 2.5 hours until a dextrose equivalent of 32 and a viscosity of 14 sec at 25% solids and 22° C. using the funnel method. The enzymes were then deactivated by heating the dispersion to 95° C. and maintaining the elevated temperature for 30 minutes. The dispersion was then cooled to room temperature and spray dried using an inlet temperature of 200° C., an outlet temperature of 100° C. and a feed rate of 65 ml/min.

Example 3 - Encapsulation of Vitamin E a. 165 grams of the starch of example 2b were dispersed in 670 grams water in a high dispersion mill. The temperature was raised to 60° C. until the starch dissolution appeared complete and then was lowered to 40° C. 165 g of Vitamin E was added and emulsified at high speed for approximately three minutes. The emulsion was spray dried to a powder which contained 50% of 1000 IU Vitamin E.

b. Example 3a was repeated using the starch of example 2a.

c. Example 3a was repeated using a zero bloom fish gelatin.

d. Example 3a was repeated using CAPSUL® starch, an encapsulating starch commercially available from National Starch and Chemical Company in Bridgewater, N.J.

Example 4 - Use of the Modified Starch in a Vitamin E Tablet

The encapsulated vitamin E of Example 3a was made into compressed tablets.

| Ingredient | Amount (mg) |
| --- | --- |
| Example 3a encapsulated vitamin E | 4000.0 |
| Magnesium Stearate[1] | 25.0 |
| Amorphous fumed silica[2] | 25.0 |
| Microcrystalline cellulose[3] | 950.0 |

[1]Magnesium stearate is commercially available from Witco.
[2]Amorphous fumed silica is commercially available under the tradename Cab-O-Sil M5 P from Cabot.
[3]Microcrystalline cellulose is commercially available under the tradename Avicel PH102 from FMC.

The ingredients were dry blended, 500 mg portions were weighed out and loaded into the press to form tablets using a Riva Piccola 10-station lab scale press at 600, 1500, and 5900 pounds force.

The hardness of these tablets were tested using a Pharmatron Model 6d Table Tester and disintegration was tested using an Erweka ZT71 Disintegration Tester. The results are listed below in Table 1.

TABLE I

| Compression Force (lbs). | Hardness (kP) | Disintegration (hh:mm:ss) |
| --- | --- | --- |
| 600 | 4.5 | 0:24:33 |
| 1500 | 4.0 | 1:36:01 |
| 5900 | 3.1 | 1:04:16 |

As can be seen from Table 1, the encapsulating starch of the present invention provides good compressibility and suitable tablet hardness.

Example 5 - Use of the Modified Starch in a Vitamin E Tablet

Example 4 was repeated using the following formulation:

| Ingredient | Amount (mg) |
| --- | --- |
| Encapsulated Vitamin E | 4450.0 |
| Magnesium Stearate[1] | 25.0 |
| Amorphous fumed silica[2] | 25.0 |
| Microcrystalline cellulose[3] | 500.0 | a. The encapsulated Vitamin E of example 3a was used. The results are listed below in Table II.
b. The encapsulated Vitamin E of example 3b was used. The results are listed below in Table II.
c. The encapsulated Vitamin E of example 3c was used. The results are listed below in Table II.
d. The encapsulated Vitamin E of example 3d was used. The results are listed below in Table II.

TABLE II

| Example | Compression force (lbs) | Hardness (kP) | Disintegration (hh:mm:ss) |
| --- | --- | --- | --- |
| 5a | 573 | 5.6 | 0:49:16 |
|  | 1695 | 6.1 | 0:40:20 |
|  | 4691 | 5.6 | 0:35:24 |
| 5b | 494 | 3.3 | 0:23:01 |
|  | 1835 | 3.7 | 0:16:43 |
|  | 4466 | 3.6 | 0:16:47 |
| 5c | 773 | 4.7 | 0:25:59 |
|  | 1770 | 4.6 | 0:24:25 |
|  | 4417 | 5.8 | 0:22:01 |
| 5d | 467 | 1.5 | 0:10:38 |

TABLE II-continued

| Example | Compression force (lbs). | Hardness (kP) | Disintegration (hh:mm:ss) |
|---|---|---|---|
| | 877 | 1.3 | 0:16:04 |
| | 4156 | 1.1 | 0:09:34 |

As can be seen from Table II, the encapsulating starches of the present invention provide good compressibility and suitable tablet hardness. In many cases, the present invention was at least comparable to the standard gelatin. Further, different hardnesses may be achieved by varying the formulation and the compression force.

Example 6 - Use of the Modified Starch in a Vitamin E Tablet

Example 4 was repeated using the following formulation:

| Ingredient | Amount (mg) |
|---|---|
| Encapsulated Vitamin E | 4700.0 |
| Magnesium Stearate[1] | 25.0 |
| Amorphous fumed silica[2] | 25.0 |
| Microcrystalline cellulose[3] | 250.0 | a. The encapsulated Vitamin E of example 3a was used. The results are listed below in Table III.
b. The encapsulated Vitamin E of example 3b was used. The results are listed below in Table III.
c. The encapsulated Vitamin E of example 3c was used. The results are listed below in Table III.
d. The encapsulated Vitamin E of example 3d was used. The results are listed below in Table III.

TABLE III

| Example | Compression force (lbs). | Hardness (kP) | Disintegration (hh:mm:ss) |
|---|---|---|---|
| 6a | 477 | 3.0 | 0:29:35 |
| | 1293 | 3.26 | 0:35:38 |
| | 5089 | 3.12 | 0:26:13 |
| 6b | 566 | 1.4 | 0:11:29 |
| | 1386 | 1.68 | 0:13:33 |
| | 5322 | 1.28 | 0:11:46 |
| 6c | 565 | 1.34 | 0:23:21 |
| | 1223 | 1.92 | 0:24:39 |
| | 5543 | 2.16 | 0:18:46 |
| 6d | 504 | 0.32 | 0:11:53 |
| | 1627 | 0.46 | 0:13:55 |
| | 5326 | 0.18 | 0:15:28 |

As can be seen from Table III, the encapsulating starches of the present invention provide good compressibility and suitable tablet hardness. In many cases, the present invention was at least comparable to the standard gelatin. Further, different hardnesses may be achieved by varying the formulation and the compression force.

Example 7 - Encapsulation of Orange Oil 240 grams of the modified starch prepared in Example 2b was dispersed in 600 ml water in a high dispersion mill. The temperature was raised to 60° C. until the starch dissolution appeared complete and then was lowered to 40° C. 160 g of a single pressed orange oil commercially available from Givaudan-Roure was added and emulsified at high speed for approximately three minutes. The emulsion was spray dried to a powder.

Example 8 - Preparation of an Orange Oil Tablet and Its Oxidation Resistance 500 mg portions of the encapsulated orange oil of Example 7 were weighed out and loaded into the press to form tablets using a Riva Piccola 10-station lab scale press at 2500 pounds force.

The oxidation resistance of the tablet was tested by re-emulsifying 100 mg of the tablet in 2 ml water. The samples were analyzed using static headspace - GC/FID to determine the level of components indicative of limonene (orange oil) oxidation. The results are shown in Table IV below.

| Tablet | % limonene epoxide | % carvone | % carveol |
|---|---|---|---|
| 1 | 0.26 | 0.36 | 0.40 |
| 2 | 0.29 | 0.30 | 0.41 |

As can be seen from Table IV, the oxidation of the tabletted orange oil was low, showing that the encapsulating starch provides excellent oxidation resistance in a tablet.

We claim:

1. A tablet comprising
   a) an encapsulating agent comprising a modified starch comprising a starch derivative containing a hydrophobic group or both a hydrophobic and a hydrophilic group which has been degraded by at least one enzyme capable of cleaving the 1,4-linkages of the starch molecule from the non-reducing ends to produce short chained saccharides; and
   b) an active agent.

2. The tablet of claim 1, wherein the starch is degraded to a dextrose equivalent of from about 20 to about 80.

3. The tablet of claim 2, wherein the starch is degraded to a dextrose equivalent of from about 20 to about 80.

4. The tablet of claim 1, wherein the enzyme is selected from the group consisting of β-amylase, glucoamylase, maltogenase, pullulanase, exo-alpha-1,4-glucosidase, exo-1,4-alpha-D-glucan maltotetrahydrolase, and exo-1,4-alpha-D glucan maltohexahydrolase.

5. The tablet of claim 4, wherein the enzyme is β-amylase or glucoamylase.

6. The tablet of claim 1, wherein the starch has a viscosity of less than about 30 seconds as measured by the funnel method.

7. The tablet of claim 6, wherein the starch has a viscosity of from about 8 to about 25 seconds.

8. The tablet of claim 7, wherein the starch has a viscosity of from about 8 to about 15 seconds.

9. The tablet of claim 1, wherein the starch derivative is gelatinized and the hydrophobic group comprises an alkyl, or an alkenyl group which contains at least five carbon atoms or an aralkyl or aralkenyl group which contains at least six carbon atoms.

10. The tablet of claim 9, wherein the starch is gelatinized and has been derivatized by treatment with at least about 0.1% octenyl succinic acid anhydride on a starch dry weight basis.

11. The tablet of claim 1, wherein the active agent is selected from the group consisting of a vitamin, a pharmaceutical, a pesticide, an oil, a protein, a fat, a flavor, a color, a catalyst, and a fragrance.

12. The tablet of claim 11, wherein the active agent is selected from the group consisting of a botanical oil, an essential oil; Vitamin A, Vitamin D, Vitamin E, Vitamin K; a peptide, an amino acid, an enzyme; and an oil soluble pharmaceutical, oil soluble pesticide.

13. The tablet of claim 12, wherein the active agent is Vitamin E.

14. The tablet of claim 1, wherein the tablet has a hardness of at least about 3 kilopascals.

15. The tablet of claim 14, wherein the tablet has a hardness of at least about 4 kilopascals.

16. A tablet comprising
   a) an encapsulating agent comprising a modified starch comprising a starch derivative containing a hydrophobic group or both a hydrophobic and a hydrophilic group and at least one compound selected from the group consisting of a monosaccharide, a disaccharide, an oligosaccharide, and a maltodextrin, said encapsulating agent being capable of achieving a 40% active agent load; and
   b) an active agent.

* * * * *